July 26, 1955
J. SPEK
Plant Pat. 1,407
ROSE PLANT
Filed Nov. 1, 1954
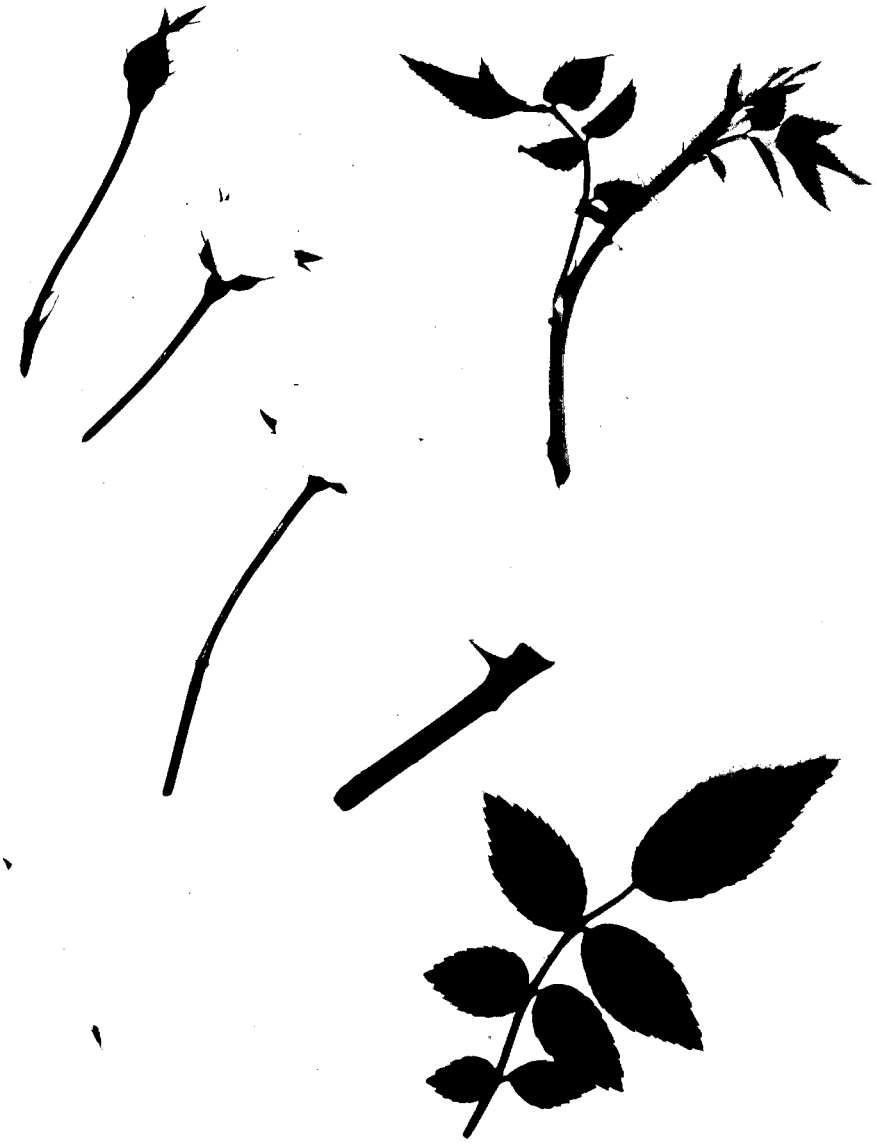
Inventor.
Jan Spek
By: Cobb & Cobb
Attorneys.

United States Patent Office

Plant Pat. 1,407

Patented July 26, 1955

1,407

ROSE PLANT

Jan Spek, Boskoop, Netherlands, assignor to Jackson & Perkins Company, Newark, N. Y., a corporation of New York Application November 1, 1954, Serial No. 466,244

1 Claim. (Cl. 47—61)

The present invention relates to a new and distinct variety of rose plant of the miniature class, which was originated by me by crossing an unpatented miniature rose named "Perla de Montserrat" with an unnamed and unpatented Polyantha seeding.

The primary objective of this cross was to produce a new white miniature rose which would be very free-blooming, which retains its foliage throughout the summer, and which retains a dwarf habit of growth and does not grow tall as it matures. This objective was fully achieved, as evidenced by the fact that my new variety does not attain a height greater than 8 inches, retains clean foliage throughout the growing season, blooms profusely, and bears flowers of a distinctive color and which are characterized by a pale flesh tinge in the bud stage, but are very white in the open flowers. This unique combination of characteristics definitely distinguishes my new variety from its parents, as well as from any other variety of rose of the miniature type of which I am aware.

Asexual reproduction of my new variety by own-rooted cuttings at Boskoop, Holland, and at Newark, N. Y., U. S. A., shows that the foregoing characteristics and distinctions come true to form and are established and transmitted through succeeding propagations.

The accompanying drawing shows typical specimens of the foliage, stems and flowers of my new variety in different stages of development, and as depicted in color as nearly true as it is reasonably possible to make the same in a color illustration of this character.

The following is a detailed description of my new variety, with color terminology in accordance with Ridgway's Color Standards and Nomenclature:

Parentage: Seeding.
- *Seed parent.*—"Perla de Montserrat."
- *Pollen parent.*—An unnamed Polyantha seedling.

Classification:
- *Botanic.*—Hybrid Chinensis Minima.
- *Commercial.*—Miniature.

FLOWER (Observations made in a greenhouse at Newark, New York, U. S. A., in the late morning, in the early part of the month of July.)

Blooming habit: Profuse. Recurrent—intermittent.

Bud:
- *Size.*—Very small.
- *Form.*—Short, with flat top; is not affected by wet or hot weather.
- *Color.*—When sepals first divide—Pale Yellow Green, Plate 6. When petals begin to unfurl—White, Plate 53. When half blown: inside of petals—White, Plate 53, with outer edges of petals Pale Flesh Color, Plate 14; reverse of petals—White, Plate 53.
- *Sepals.*—Serrated; branched; curl back when petals begin to unfurl. Color: inside—Kildare Green, Plate 31; outside—Light Cress Green, Plate 31.
- *Calyx.*—Color—Light Cress Green, Plate 31. Shape—Funnel. Size—small. Aspect—smooth. Odor when rubbed—none.
- *Peduncle.*—Length—short; nested in foliage. Aspect — smooth. Strength — erect; slender. Color—Lettuce Green, Plate 5.
- *Opening.*—Opens up well; is not affected by adverse weather conditions.

Bloom:
- *Size.*—Small; average size when fully expanded—¾ inch.
- *Borne.*—Singly and in irregular clusters.
- *Stems.*—Short; normal strength.
- *Form (when first open).*—Cupped. Permanence—flattens; outer petals curl back slightly.
- *Petalage.*—Very double (many petals and stamens hidden); number of petals under normal conditions—from 40 to 45.
- *Color.*—Center of flower—White, Plate 53. Outer petals—White, Plate 53. Base of petals (aiglet)—Marguerite Yellow, Plate 30. Inside of petals—White, Plate 53. Reverse of petals—White, Plate 53. General tonality from a distance—White, Plate 53.
- *Discoloration.*—General tonality at end of first day—White, Plate 53. Second day—White, Plate 53. Third day—White, Plate 53.

Petals:
- *Texture.*—Thin; is not affected by wet or hot weather.
- *Appearance.*—Inside—satiny. Outside—shiny.
- *Form.*—Oval.
- *Arrangement.*—Irregular.
- *Petaloids in center.*—Few; small.
- *Persistence.*—Drop off cleanly.
- *Fragrance.*—Moderate. Nature—tea (average hybrid tea scent).
- *Lasting quality.*—On the plant—long. As cut flower—long.

GENITAL ORGANS

Stamens, anthers: None.
Stamens, filaments (threads): None.
Pollen: None.
Styles: Columnar; uneven length; short; thin.
Stigmas: Color—Light Lumiere Green, Plate 17.
Ovaries: All enclosed in calyx.
Hips: None.
Seeds: None.

PLANT

Form: Bush.
Growth: Dwarf; not more than 8 inches in height; compact.
Foliage: 5 to 7 leaflets.
- *Size.*—Small.
- *Quantity.*—Normal.
- *Color.*—New foliage: upper side—Spinach Green, Plate 5, lightly overcast with Oxblood Red, Plate 1; under side—Yellowish Oil Green, Plate 5, lightly overcast with Garnet Brown, Plate 1. Old foliage: upper side—Varley's Green, Plate 18, with mid-rib and serrations Vandyke Red, Plate 13; under side—Cress Green, Plate 31.
- *Shape.*—Oval pointed.
- *Texture.*—Upper side—glossy. Under side—smooth.
- *Ribs and veins.*—Ordinary.
- *Edge.*—Serrated (saw-toothed).
- *Serration.*—Single; small.

*Leaf stem.*—Color—Light Cress Green, Plate 31. Under side—prickles.

*Stipules.*—Short; bearded.

Wood:

*New wood.*—Color—Absinthe Green, Plate 31. Bark—smooth.

*Old wood.*—Color—Yew Green, Plate 31. Bark—smooth.

Thorns:

*Thorns.*—Quantity: on main stalks from base—few; on laterals from stalk—few. Form—narrow base; medium length; hooked downward. Color (when young)—Eugenia Red, Plate 13. Position—irregular.

*Prickles.*—Quantity: on main stalks—none; on laterals—none.

*Short needles.*—Quantity: on main stalks—none; on laterals—none.

I claim:

A new and distinct variety of rose plant of the miniature class, substantially as herein shown and described, characterized paticularly as to novelty by the retention of its low plant growth throughout its entire life, its clean foliage and the retention thereof throughout the growing season, its very free-blooming habit, and the distinctive color of its flowers which in the bud stage are tinged Pale Flesh color, but in the open flower stage are very White.

No references cited.